US012751677B2

(12) United States Patent
Okajima et al.

(10) Patent No.: US 12,751,677 B2
(45) Date of Patent: Oct. 6, 2026

(54) X-RAY CT APPARATUS

(71) Applicant: Canon Kabushiki Kaisha, Tokyo (JP)

(72) Inventors: Yuji Okajima, Nasushiobara (JP); Shuya Nambu, Nasushiobara (JP); Hiroaki Miyazaki, Otawara (JP)

(73) Assignee: Canon Kabushiki Kaisha, Tokyo (JP)

(*) Notice: Subject to any disclaimer, the term of this patent is extended or adjusted under 35 U.S.C. 154(b) by 268 days.

(21) Appl. No.: 18/491,857

(22) Filed: Oct. 23, 2023

(65) Prior Publication Data

US 2024/0130695 A1 Apr. 25, 2024
US 2024/0225567 A9 Jul. 11, 2024

(30) Foreign Application Priority Data

Oct. 25, 2022 (JP) ................................ 2022-170698

(51) Int. Cl.
*A61B 6/03* (2006.01)
*A61B 6/00* (2024.01)
*A61B 6/42* (2024.01)

(52) U.S. Cl.
CPC ............ *A61B 6/032* (2013.01); *A61B 6/4241* (2013.01); *A61B 6/5205* (2013.01)

(58) Field of Classification Search
CPC ..................................................... A61B 6/032
See application file for complete search history.

(56) References Cited

U.S. PATENT DOCUMENTS 10,176,603 B2 1/2019 Rigie et al.
2015/0043796 A1* 2/2015 Rigie .................. G06T 3/4061 382/131

FOREIGN PATENT DOCUMENTS

| | | | |
|---|---|---|---|
| JP | 2011-206536 | A | 10/2011 |
| JP | 2014-014445 | A | 1/2014 |
| JP | 2015-33582 | A | 2/2015 |
| JP | 2018-175866 | A | 11/2018 |
| JP | 2022-26909 | A | 2/2022 |

OTHER PUBLICATIONS

Japanese Office Actin dated Jul. 29, 2026, issued in Japanese Patent Application No. 2022-170698 (with English translation).

* cited by examiner

*Primary Examiner* — Edwin C Gunberg
(74) *Attorney, Agent, or Firm* — Oblon, McClelland, Maier & Neustadt, L.L.P.

(57) ABSTRACT

An X-ray CT apparatus according to an embodiment includes a photon-counting X-ray detector including a plurality of pixels and processing circuitry configured to acquire first data in a resolution priority mode from a first pixel set out of the pixels, acquire second data in an energy decomposition mode from a second pixel set, which is different from the first pixel set, out of the pixels at sampling intervals longer than those of the resolution priority mode, and generate third data based on the first data and the second data.

14 Claims, 10 Drawing Sheets

| | | | | |
|---|---|---|---|---|
| COUNT DATA OF VIEW 1-4 (>E1 [keV]) | COUNT DATA OF VIEW 1-4 (>E2 [keV]) | COUNT DATA OF VIEW 1-4 (>E3 [keV]) | COUNT DATA OF VIEW 1-4 (>E4 [keV]) | INCI-DENTAL INFOR-MATION |

X-RAY CT APPARATUS

CROSS-REFERENCE TO RELATED APPLICATIONS

This application is based upon and claims the benefit of priority from Japanese Patent Application No. 2022-170698, filed on Oct. 25, 2022; the entire contents of which are incorporated herein by reference.

FIELD

Embodiments described herein relate generally to an X-ray computed tomography (CT) apparatus.

BACKGROUND

In an X-ray CT apparatus, a signal detected at each pixel of an X-ray detector is read at a predetermined sampling rate, and CT image data is generated from the read signal. While information of more irradiation angles (views) can be acquired to improve the resolution as the sampling rate is increased, the size of data increases, and time required for transmission of the data also increases. That is, time required until an image is output increases when the resolution of the image is to be improved by increasing the sampling rate.

DETAILED DESCRIPTION

An X-ray CT apparatus according to an embodiment includes a photon-counting X-ray detector including a plurality of pixels and processing circuitry configured to acquire first data in a resolution priority mode from a first pixel set out of the pixels, acquire second data in an energy decomposition mode from a second pixel set, which is different from the first pixel set, out of the pixels at sampling intervals longer than those of the resolution priority mode, and generate third data based on the first data and the second data.

Hereinafter, embodiments of the X-ray CT apparatus will be explained in detail with reference to the accompanying drawings.

Figure 1:
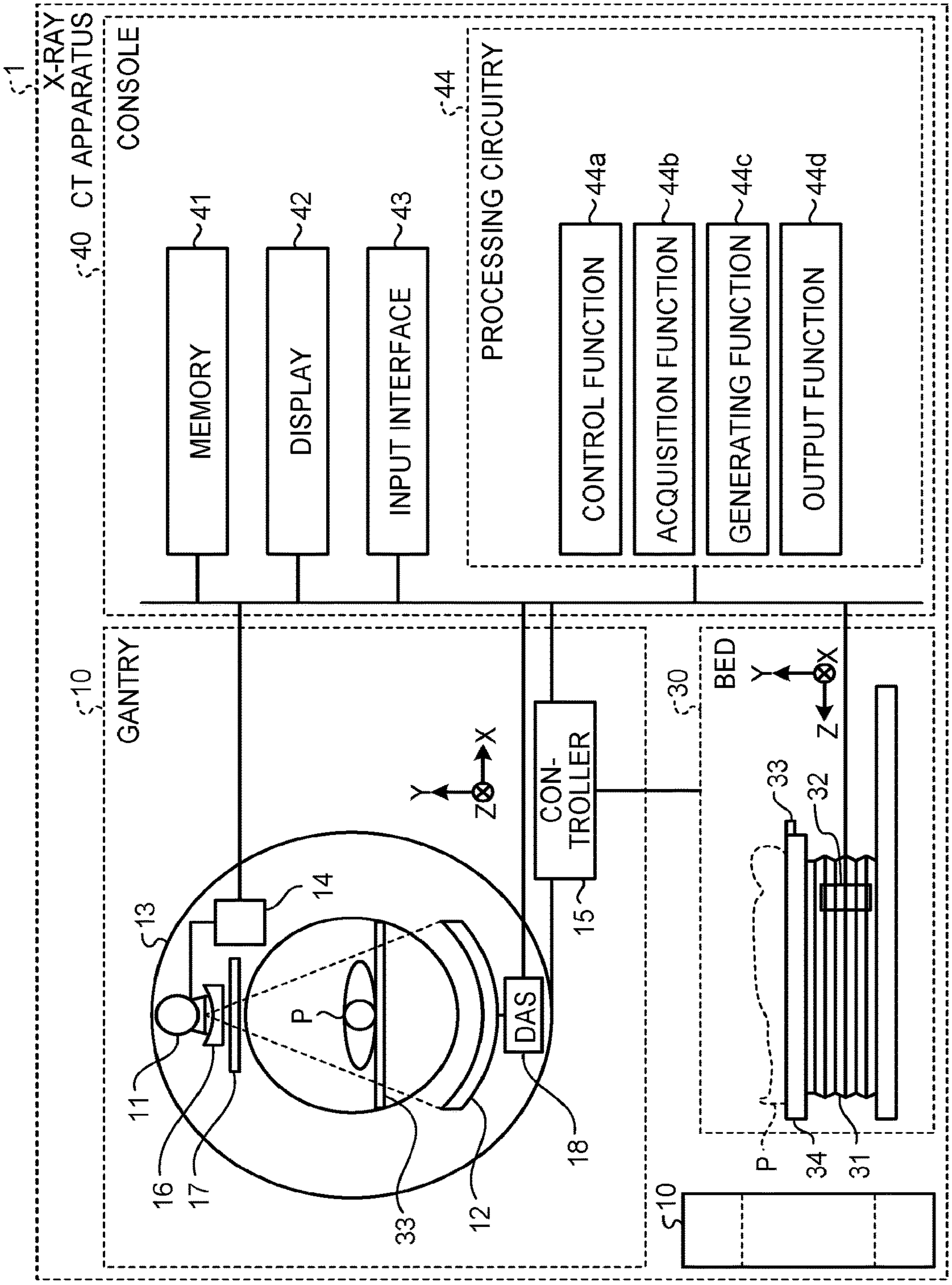
FIG. 1 is a block diagram illustrating an example of a configuration of an X-ray CT apparatus according to a first embodiment.

In the present embodiment, an X-ray CT apparatus 1 illustrated in FIG. 1 will be explained as an example. FIG. 1 is a block diagram illustrating an example of a configuration of the X-ray CT apparatus 1 according to a first embodiment. For example, the X-ray CT apparatus 1 includes a gantry 10, a bed 30, and a console 40.

In FIG. 1, a rotation axis of a rotating frame 13 in a non-tilted state or a longitudinal direction of a tabletop 33 of the bed 30 are defined as a Z-axis direction. Moreover, an axial direction that is perpendicular to the Z-axis direction, and is horizontal with respect to a floor surface is defined as an X-axis direction. Furthermore, an axial direction that is perpendicular to the Z-axis direction, and is perpendicular to the floor surface is defined as a Y-axis direction. FIG. 1 illustrates the gantry 10 from multiple directions for explanation's sake, and illustrates a case in which the X-ray CT apparatus 1 has a single unit of the gantry 10.

The gantry 10 includes an X-ray tube 11, an X-ray detector 12, a rotating frame 13, an X-ray high-voltage device 14, a controller 15, a wedge 16, a collimator 17, and a data acquisition system (DAS) 18.

The X-ray tube 11 is a vacuum tube having a cathode (filament) that generates thermions, and an anode (target) that receives collision of thermions to generate X-rays. The X-ray tube 11 generates X-rays to be irradiated to a subject P by irradiating thermions from the cathode toward the anode with a high voltage applied from the X-ray high-voltage device 14.

The X-ray detector 12 includes plural detecting devices (pixels), and detects an X-ray that has been irradiated from the X-ray tube 11 and has passed through the subject P, to output a signal corresponding to a detected X-ray amount to the DAS 18. The X-ray detector 12 has plural detecting device arrays in which plural detecting devices are aligned, for example, in a channel direction along an arc centered around a focal point of the X-ray tube 11. The X-ray detector 12 has, for example, a structure in which the detecting device arrays having plural detecting devices aligned in the channel direction are arranged in a column direction (slice direction, row direction) in plurality.

In the present embodiment, a case in which the X-ray detector 12 is a photon counting detector will be explained. In this case, the X-ray detector 12 is, for example, a direct conversion detector that converts an incident X-ray photon directly into an electrical signal. As the direct detection detector, for example, a semiconductor diode in which electrodes are arranged on both ends of a semiconductor is applicable. X-ray photons that have entered the semiconductor are converted into electron hole pairs. The number of electron-hole pairs generated by entrance of a single X-ray photon depends on the energy of the incident X-ray photon. An electron and a hole are attracted to the pair of electrodes formed at both ends of the semiconductor. The pair of electrodes generate electrical pulses having heights corresponding to the charge of the electron-hole pair. A single electrical pulse has a peak value according to the energy of the incident X-ray photon.

The rotating frame 13 is a ring-shaped frame that supports the X-ray tube 11 and the X-ray detector 12 in an opposing manner, and that rotates the X-ray tube 11 and the X-ray detector 12 by the controller 15. For example, the rotating frame 13 is a casting made from an aluminum material. The rotating frame 13 can also support the X-ray high-voltage device 14, the wedge 16, the collimator 17, the DAS 18, and the like in addition to the X-ray tube 11 and the X-ray detector 12. Hereinafter, the rotating frame 13 and a portion that rotates along with the rotating frame 13 in the gantry 10 are denoted as rotor also. Moreover, a portion that does not rotate in the gantry 10 is denoted as stator also. The stator supports the rotor.

The controller 15 performs control of operation of the gantry 10 and the bed 30. The wedge 16 is an X-ray filter to adjust an amount of X-rays irradiated from the X-ray tube 11. The collimator 17 is an X-ray aperture to narrow an irradiation range of an X-ray that has passed through the wedge 16. The aperture range of the collimator 17 may be mechanically adjustable.

The DAS 18 acquires count data (counting data) that indicates a count of X-ray photons detected by the X-ray detector 12 for one or more energy bins, for example, in accordance with a control signal from the controller 15. The count data of plural energy bins corresponds to an energy spectrum of an incident X-ray to the X-ray detector 12 distorted according to response characteristics of the X-ray detector 12. The DAS 18 outputs detection data based on a digital signal to the console 40. The detection data is a digital value of the count data that is identified based on a channel number of an X-ray detecting device of its generation origin, a column number, and a view number indicating an acquired view. The view number is a number that varies according to rotation of the rotating frame 13, and is a number that is incremented, for example, according to rotation of the rotating frame 13. Therefore, the view number is information indicating a rotation angle of the X-ray tube 11. A view period is a period that fits between a rotation angle corresponding to one view number and a rotation angle corresponding to a next view number.

The DAS 18 may detect a switch of views based on a timing signal input by the controller 15, may detect it based on an internal timer, or may detect it based on a signal acquired from a sensor not illustrated. In the case of performing full scanning, when X-rays are continuously emitted by the X-ray tube 11, the DAS 18 acquires a detection data set of all circumferences (360 degrees). In the case of performing half scanning, when X-rays are continuously emitted by the X-ray tube 11, the DAS 18 acquires detection data corresponding to half circumferences (180 degrees).

The bed 30 is a unit to lay and to move the subject P to be scanned by CT scanning thereon, and includes a base 31, a bed driving device 32, a tabletop 33, and a supporting frame 34. The base 31 is a casing that supports the supporting frame 34 movably in a vertical direction. The bed driving device 32 is a driving mechanism that moves the tabletop 33 on which the subject P is laid in a longitudinal direction of the tabletop 33, and includes a motor, an actuator, and the like. The tabletop 33 arranged on an upper surface of the supporting frame 34 is a plate on which the subject P is laid. The bed driving device 32 may move the supporting frame 34, in addition to the tabletop 33, in the longitudinal direction of the tabletop 33.

The console 40 includes a memory 41, a display 42, an input interface 43, and processing circuitry 44. The console 40 is explained as a separate unit from the gantry 10, but the gantry 10 may include the console 40 or a part of the respective components of the console 40.

The memory 41 is implemented by, for example, a semiconductor memory device, such as a random access memory (RAM) and a flash memory, a hard disk, an optical disk, and the like. For example, the memory 41 stores projection data acquired by CT scanning, and CT image data that is reconstructed based on the projection data. Moreover, the memory 41 stores a program for a circuit included in the X-ray CT apparatus 1 to implement its function. The memory 41 may be implemented by a server group (cloud) that is connected to the X-ray CT apparatus 1 through a network.

The display 42 displays various kinds of information under control of the processing circuitry 44. For example, the display 42 displays a graphical user interface (GUI) to accept various kinds of instructions, settings, and the like from a user through the input interface 43. Furthermore, the display 42 displays an image for display that is generated based on CT image data. For example, the display 42 is a liquid crystal display or a cathode ray tube display. The display 42 may be a desktop type, or may be constituted of a tablet terminal that can perform wireless communication with the processing circuitry 44, or the like.

The input interface 43 accepts various kinds of input operations from a user, and converts the accepted input operation into an electrical signal, to output to the processing circuitry 44. For example, the input interface 43 is implemented by a mouse, a keyboard, a trackball, a switch, a button, a joystick, a touch pad without which input operation is performed by touching an operating surface, a touch screen in which a display screen and a touch pad are integrated, a non-contact input circuit using an optical sensor, a sound input circuit, and the like. The input interface 43 may be constituted of a tablet terminal that is capable of wireless communication with the processing circuitry 44, or the like. Moreover, the input interface 43 may be constituted of a circuit that accepts an input operation from a user by motion capture system. As an example, by processing a signal acquired through a tracker or an acquired image of a user, the input interface 43 can accept a body movement, a line of sight, and the like of the user as an input operation. Furthermore, the input interface 43 is not limited to those including a physical operating part, such as a mouse and a keyboard. For example, a processing circuit of an electrical signal that receives an electrical signal corresponding to an input operation from an external input device arranged separately from the X-ray CT apparatus 1 and that outputs this electrical signal to the processing circuitry 44 is also included in examples of the input interface 43.

The processing circuitry 44 controls overall operation of the X-ray CT apparatus 1 by performing a control function 44*a*, an acquisition function 44*b*, a generating function 44*c*, and an output function 44*d*. For example, the processing circuitry 44 functions as the control function 44*a* by reading and executing a program corresponding to the control function 44*a* from the memory 41. Similarly, the processing circuitry 44 functions as the acquisition function 44*b*, the generating function 44*c*, and the output function 44*d*. The acquisition function 44*b* is an example of an acquiring unit. The generating function 44*c* is an example of a generating unit.

For example, the control function 44*a* controls the acquisition function 44*b*, the generating function 44*c* in accordance with an instruction from a user accepted through the input interface 43. Moreover, the acquisition function 44*b* performs CT scanning on the subject P, and acquires detection data. For example, the acquisition function 44*b* supplies a high voltage to the X-ray tube 11 by controlling the X-ray high-voltage device 14. Thus, the X-ray tube 11 generates an X-ray to be irradiated to the subject P. Furthermore, the acquisition function 44*b* moves the subject P into a bore of the gantry 10 by controlling the bed driving device 32. Moreover, the acquisition function 44*b* controls distribution of X-rays irradiated to the subject P by adjusting a position of the wedge 16, and an aperture size and a position of the collimator 17.

Furthermore, the acquisition function 44*b* acquires first data in a resolution priority mode from a first pixel set out of plural pixels in the X-ray detector 12, and acquires second data in an energy decomposition mode from second pixel set that is different from the first pixel set, by controlling operation of the controller 15 and the DAS 18. Moreover, the generating function 44*c* generates third data based on the first data and the second data. Details of processing by the acquisition function 44*b* and the generating function 44*c* will be described later.

The output function 44*d* controls output of various kinds of data. For example, the output function 44*d* performs control of display in the display 42. For example, the output function 44*d* converts CT image data into a display image, such as arbitrary cross-sectional image or a rendered image in an arbitrary viewing direction, based on an input operation accepted from a user through the input interface 43, to display on the display 42.

In the X-ray CT apparatus 1 illustrated in FIG. 1, the respective processing functions are stored in the memory 41 in a form of computer-executable program. The processing circuitry 44 is a processor that implements a function corresponding to each program by reading and executing the program from the memory 41. In other words, the processing circuitry 44 that has read the program is to have the function corresponding to the read program.

Although it has been explained that the control function 44*a*, the acquisition function 44*b*, the generating function 44*c*, and the output function 44*d* are implemented by a single unit of the processing circuitry 44 in FIG. 1, it may be configured such that plural independent processors constitute the processing circuitry 44 in combination, and a function is implemented by each processor executing a program. Moreover, the respective processing functions included in the processing circuitry 44 may be implemented by a single or plural processing circuits in a distributed or an integrated manner appropriately.

Furthermore, the processing circuitry 44 may implement the functions by using an external processor connected through a network NW. For example, the processing circuitry 44 implements the respective functions indicated in FIG. 1 by reading and executing a program corresponding to each function from the memory 41, and using a server group (cloud) connected with the X-ray CT apparatus 1 through the network NW as a computational resource.

Moreover, it has been explained that a single memory stores programs corresponding to the respective processing functions of the processing circuitry. However, embodiments are not limited thereto. For example, it may be configured such that plural memories are arranged in a distributed manner, and the processing circuitry reads a corresponding program from an individual memory.

Furthermore, instead of storing the programs in a memory, the programs may be directly installed in a processor in circuitry. In this case, the processor implements a function by reading and executing a program installed in the circuitry. For example, a program corresponding to the acquisition function 44*b* may be installed in circuitry in the DAS 18. That is, the acquisition function 44*b* may be integrated with the DAS 18.

The configuration example of the X-ray CT apparatus 1 has been explained above. With such a configuration, the X-ray CT apparatus 1 can improve the resolution while avoiding increase of time required until output of an image. Hereinafter, details of the processing by the X-ray CT apparatus 1 will be explained using FIG. 2 and FIG. 3.

Figure 2:
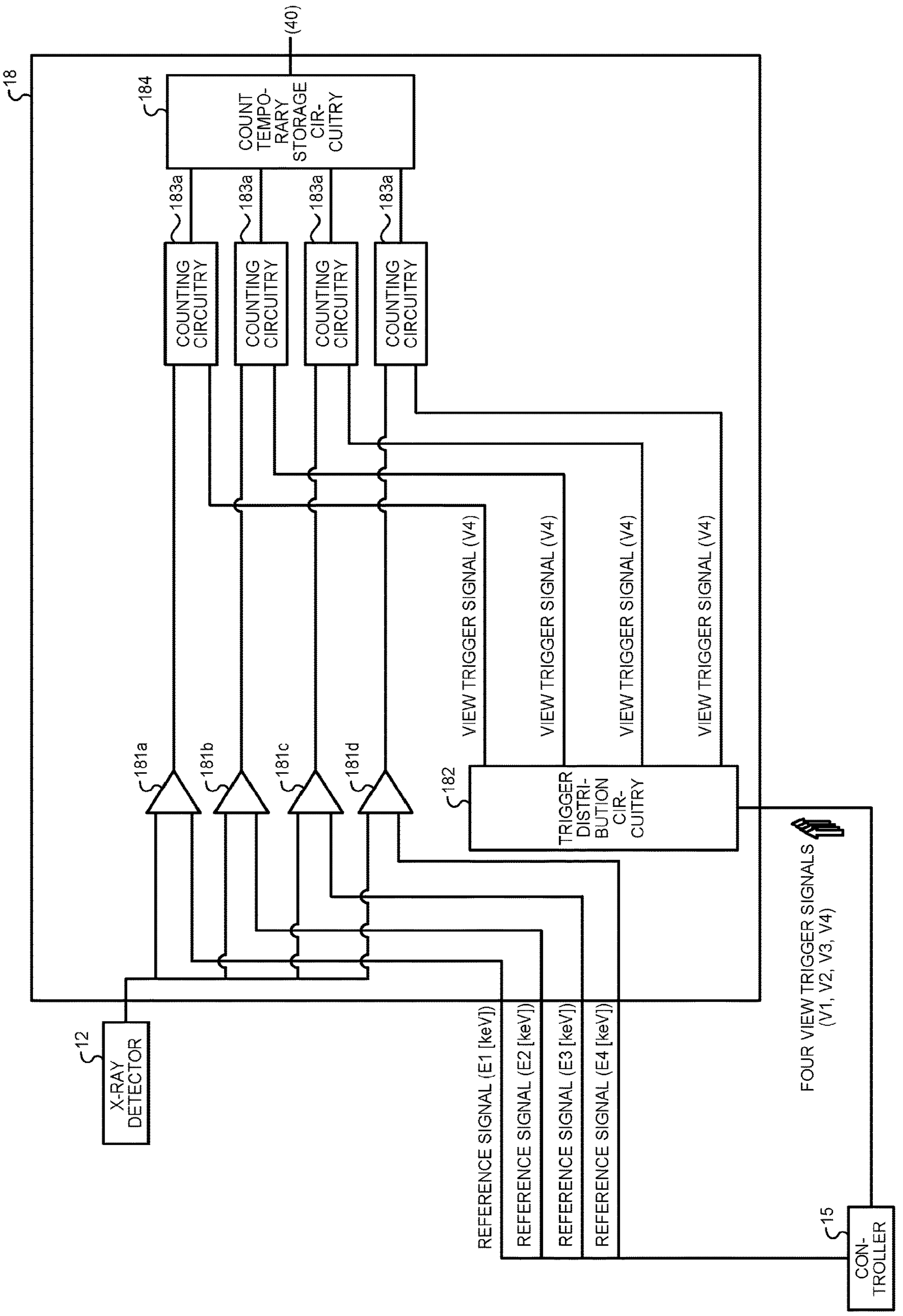
FIG. 2 is a diagram illustrating a configuration example of a DAS according to the first embodiment.
Figure 3:
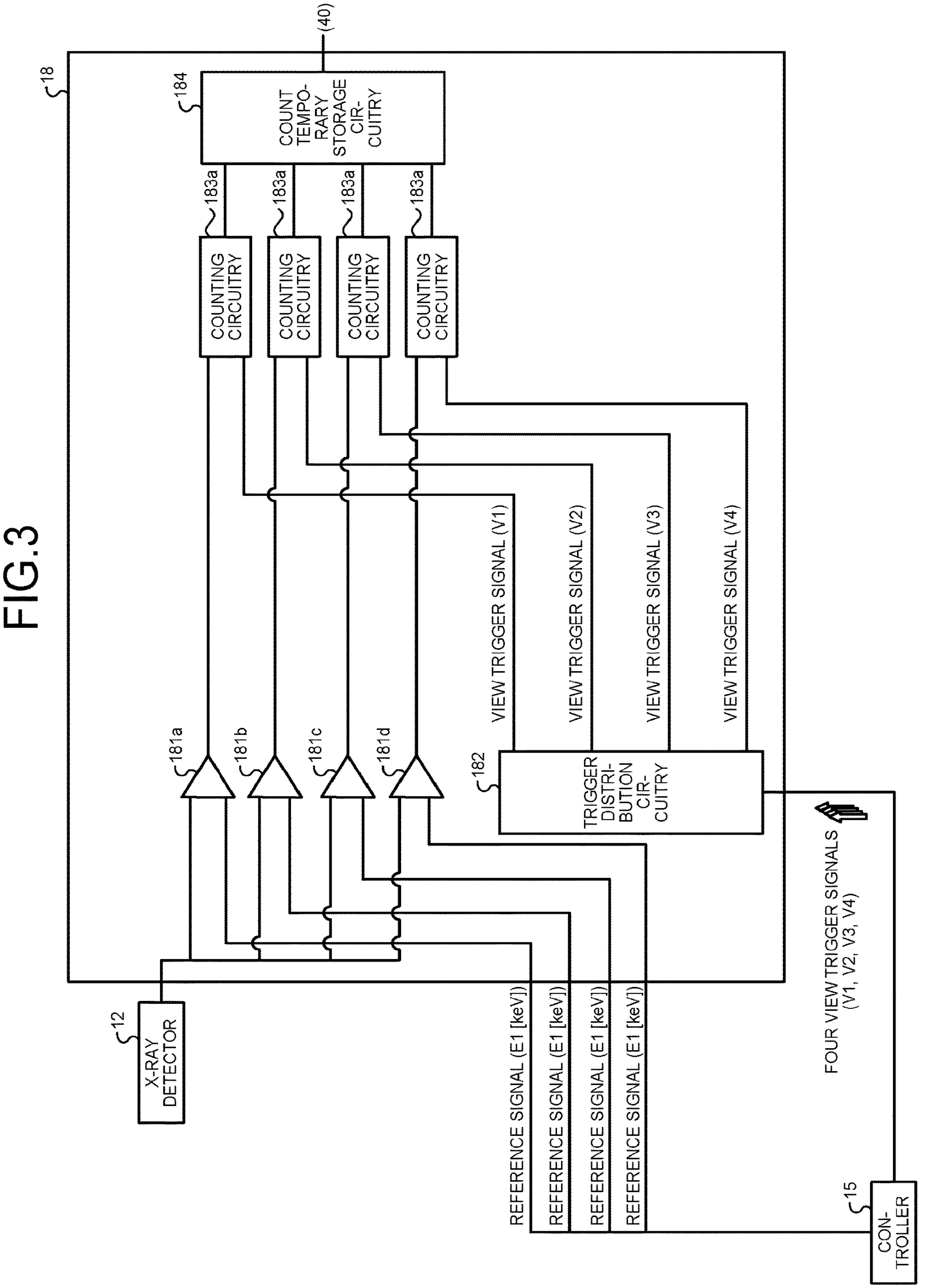
FIG. 3 is a diagram illustrating a configuration example of the DAS according to the first embodiment.

The DAS 18 includes readout channels as many as the number of channels corresponding to the number X-ray detecting devices. These readout channels are provided in parallel to the integrated circuit, such as an application specific integrated circuit (ASIC). In FIG. 2 and FIG. 3, out of the DAS 18, a configuration corresponding to one readout channel is illustrated.

The DAS 18 includes, for example, plural comparators, a trigger distribution circuitry 182, plural counting circuitry, and count temporary-storage circuitry. In FIG. 2 and FIG. 3, as the plural comparators, four comparators (a comparator 181*a*, a comparator 181*b*, a comparator 181*c*, a comparator 181*d*) are illustrated. The four comparators are connected in parallel with respect to the X-ray detector 12. Moreover, as the plural counting circuitry, four counting circuits (counting circuitry 183*a*, counting circuitry 183*b*, counting circuitry 183*c*, counting circuitry 183*d*) are illustrated. The counting circuitry 183*a* is connected to an output terminal of the comparator 181*a*. Similarly, the counting circuitry 183*b* is connected to an output terminal of the comparator 181*b*, the counting circuitry 183*c* is connected to an output terminal of the comparator 181*c*, and the counting circuitry 183*d* is connected to an output terminal of the comparator 181*d*.

That is, in the example of FIG. 2 and FIG. 3, four counting channels are arranged. In this case, it is possible to set four energy bands (energy bins). The number of counting channels can be changed arbitrarily, and for example, when n counting channels are provided, n energy bins can be set.

As illustrated in FIG. 2 and FIG. 3, the X-ray detector 12 is connected the plural comparators. To the comparators, pulse signals that are generated by incident X-rays are input from the detecting devices of the X-ray detector 12. For example, a detection electrical signal (current signal) transmitted from the detecting device of the X-ray detector 12 is amplified by a preamplifier circuitry not illustrated. The preamplifier circuit converts a current signal from a detecting device of a connection destination into a voltage signal having a voltage value (peak value) proportional to a charge amount of the current signal. Furthermore, the voltage signal output from the preamplifier is subjected to waveform shaping by the waveform shaping circuitry not illustrated. For example, the waveform shaping circuitry reduces a pulse width of the voltage signal from the preamplifier. The pulse signals, the waveform of which is shaped by the waveform shaping circuitry are input to the respective comparators.

One of input terminals of each of the comparators is connected to the X-ray detector 12 as illustrated in FIG. 2 and FIG. 3. From the one input terminal, the pulse signal described above is input. The other input terminal of each of the comparators is connected to the controller 15. From the other input terminal, a reference signal (a reference voltage value and the like) is input. The respective comparators compare the input pulse signal with the reference signal, and only when the electric charge of the pulse signal or the pulse height exceed those of the reference signal, outputs a signal to the counting circuitry.

The trigger distribution circuitry 182 distributes a view trigger signal provided by the controller 15 in accordance with trigger distribution settings provided by the acquisition function 44*b*, to provide it to each of the counting circuitry. The trigger distribution circuitry 182 may generate a view trigger signal on its own in accordance with the trigger distribution settings provided by the acquisition function 44*b*.

Each of the counting circuitry adds 1 to a count value stored in an internal memory each time a signal is input from the comparator. Each of the counting circuitry reads out data of count values (that is, count data) accumulated in the internal memory, triggered by supply of the view trigger signal from the trigger distribution circuitry 182. That is, each of the counting circuitry accumulates signals output by respective pixels of the X-ray detector 12 according to incident X-rays as the count data, and reads out the accumulated count data upon reception of the view trigger signal. Each of the counting circuitry outputs the reads read out count data to count temporary-storage circuitry 184. Moreover, each of the counting circuitry resets the count value accumulated in the internal memory to an initial value each time the view trigger signal is supplied. Thus, each of the counting circuitry counts the count value for each view.

The count data stored in the count temporary-storage circuitry 184 is appropriately transmitted to the console 40. For example, the count temporary-storage circuitry 184 outputs the stored count data to readout circuitry not illustrated at the time when the count data from all the counting circuitry are stored. The readout circuit converts the count data output from the count temporary-storage circuitry 184 into a certain data format, to transmit to the console 40. The transmitted count data is stored, for example, in the memory 41.

In the example illustrated in FIG. 2, a reference signal "E1 [keV]" is provided to the comparator 181*a* out of the plural comparators. In this case, the comparator 181*a* can count X-ray photons having an energy exceeding "E1 [keV]". Similarly, a reference signal "E2 [keV]" is provided to the comparator 181*b*, a reference signal "E3 [keV]" is provided to the comparator 181*c*, and a reference signal "E4 [keV]" is provided to the comparator 181*d*. For example, the controller 15 provides the reference signals to the respective comparators in accordance with reference signal settings provided by the acquisition function 44*b*.

Moreover, in the example in FIG. 2, a view trigger signal "V4" is equally provided to the plural counting circuitry (the counting circuitry 183*a*, the counting circuitry 183*b*, the counting circuitry 183*c*, the counting circuitry 183*d*). That is, in the example in FIG. 2, the count data is read out at the same time in the plural counting circuitry. When the view trigger signal "V4" is provided, the counting circuitry 183*a* reads out the count data of a signal input from the comparator 181*a* from the internal memory, to output to the count temporary-storage circuitry 184. Similarly, when the view trigger signal "V4" is provided, the counting circuitry 183*b* outputs the count data of a signal input from the comparator 181*b*, the counting circuitry 183*c* outputs the count data of a signal input from the comparator 181*c*, and the counting circuitry 183*d* outputs the count data of a signal input from the comparator 181*d*.

In the example illustrated in FIG. 2, the count data of the respective energy bins can be acquired. For example, by taking a difference between the count data acquired by the comparator 181*a* and the count data acquired by the comparator 181*b*, count data of an energy bin "E1 [keV] to E2 [keV]" can be acquired. Moreover, by taking a difference between the count data acquired by the comparator 181*b* and the count data acquired by the comparator 181*c*, count data of an energy bin "E2 [keV] to E3 [keV]" can be acquired. Furthermore, by taking a difference between the count data acquired by the comparator 181*c* and the count data acquired by the comparator 181*d*, count data of an energy bin "E3 [keV] to E4 [keV]" can be acquired. Moreover, the count data acquired by the comparator 181*d* is count data of an energy bin "E4 [keV] and higher". That is, in the example illustrated in FIG. 2, the count data can be acquired in the energy decomposition mode. The count data acquired in the energy decomposition mode is also denoted as second data.

On the other hand, in the example illustrated in FIG. 3, a reference signal "E1 [keV]" is equally provided to the plural comparators (the comparator 181*a*, the comparator 181*b*, the comparator 181*c*, the comparator 181*d*). That is, in the example in FIG. 3, counting is performed using a single energy "E1 [keV]" as a threshold in the plural comparators.

Moreover, in the example in FIG. 3, to the counting circuitry 183*a*, a view trigger signal "V1" is provided, to the counting circuitry 183*b*, a view trigger signal "V2" is provided, to the counting circuitry 183*c*, a view trigger signal "V3" is provided, and to the counting circuitry 183*d*, a view trigger signal "V4" is provided. That is, in the example in FIG. 3, the count data is read out in a different timing in each of the counting circuitry.

For example, first, the view trigger signal "V1" is provided to the counting circuitry 183*a*, and the count data of the counting circuitry 183*a* is read out. Next, the view trigger signal "V2" is provided to the counting circuitry 183*b*, and the count data of the counting circuitry 183*b* is read out. Next, the view trigger signal "V3" is provided to the counting circuitry 183*c*, and the count data of the counting circuitry 183*c* is read out. Next, the view trigger signal "V4" is provided to the counting circuitry 183*d*, and the count data of the counting circuitry 183*d* is read out. As described, in the example in FIG. 3, readout of the count data is performed at short sampling intervals compared to the case of FIG. 2 in which the count data is read out only in the common timing when the view trigger signal "V4" is provided.

As illustrated in FIG. 3, by reading out the count data in different timings for the respective counting circuitry, the count data can be acquired for more views. For example, when the count data acquired in the case of FIG. 2 is data corresponding to "view 1-4", the count data in the counting circuitry 183*a* corresponds to "view 1" in FIG. 3, the count data of the counting circuitry 183*b* corresponds to "view 1-2", the count data of the counting circuitry 183*c* corresponds to "view 1-3", and the count data of the counting circuitry 183*d* corresponds to "view 1-4". By taking differences among these pieces of the count data, count data of "view 1", count data of "view 2", count data of "view 3", and count data of "view 4" can be also generated. As described, in the example in FIG. 3, the temporal resolution of acquired count data improves.

When reconstruction processing of CT image data is performed, by using information of more views for the reconstruction processing, the spatial resolution of the CT image data can be improved. That is, by improving the temporal resolution of count data, the spatial resolution of the CT image data can be improved.

As described above, in the example illustrated in FIG. 3, it is possible to acquire count data in the resolution priority mode in which the temporal resolution of the count data and the spatial resolution of CT image data can be improved. The count data acquired in the resolution priority mode is also denoted as first data.

The energy decomposition mode illustrated in FIG. 2 and the resolution priority mode illustrated in FIG. 3 can be set per pixel in the X-ray detector 12, and can be switched as appropriate. Specifically, by changing the reference signal transmitted from the controller 15 to the comparators and the view trigger signal transmitted from the trigger distribution circuitry 182 to the counting circuitry, the energy decomposition mode and the resolution priority mode can be switched. For example, the acquisition function 44*b* can switch the energy decomposition mode and the resolution priority mode by changing the reference information settings to be provided to the controller 15 or the trigger distribution settings to be provided to the trigger distribution circuitry 182.

Figure 4:
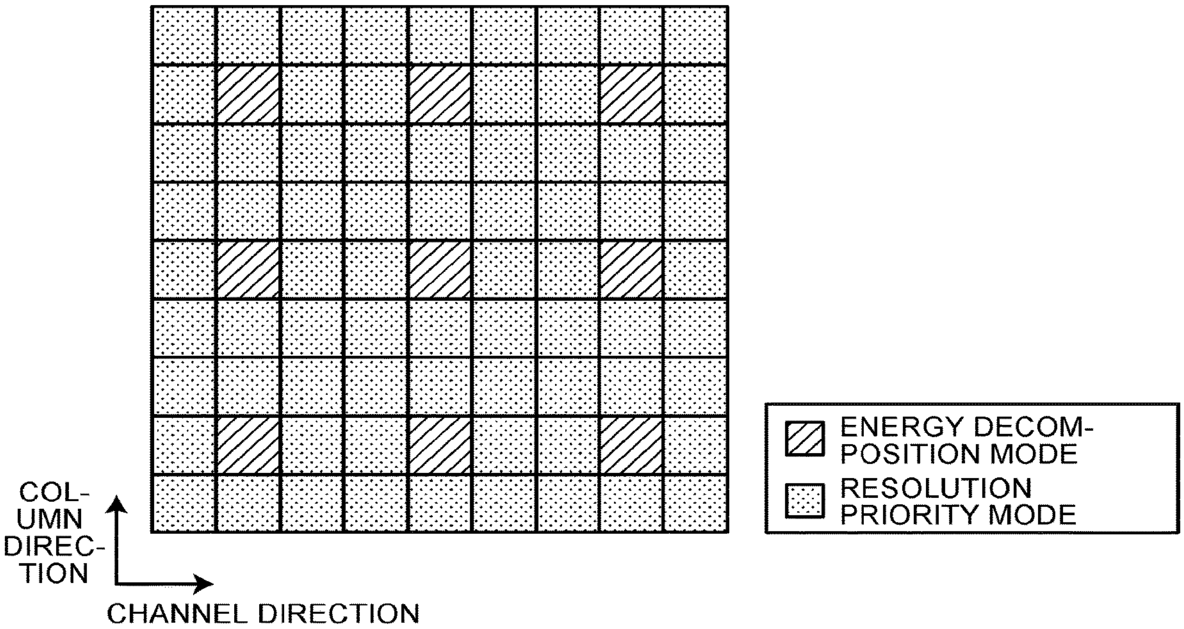
FIG. 4 is an example of a method of setting a resolution priority mode and an energy decomposition mode for each pixel according to the first embodiment.

For example, in FIG. 4, the energy decomposition mode is set for a pixel, a pixel number in a column direction of which is “3n−1” and a pixel number in a channel direction of which is “3m−1”, and the resolution priority mode is set for other pixels, where “n” and “m” are arbitrary positive integers. By thus performing CT scanning, the first data is acquired from the first pixel set for which the resolution priority mode is set, and the second data is acquired from the second pixel set for which the energy decomposition mode is set. In the case of FIG. 2 and FIG. 3, the second data to be acquired is data having energy information obtained by counting for each of the energy bins. On the other hand, the first data is high resolution data that is acquired at short sampling intervals, although it does not have the energy information of each energy bin.

The generating function 44*c* generates third data that has both high resolution and energy information by synthesizing the first data of high resolution and the second data having the energy information.

For example, the first data and the second data acquired by the acquisition function 44*b* are stored in the memory 41. The first data may be projection data that indicates a distribution of X-ray intensity on a detection plane of the X-ray detector 12, or may be CT image data subjected to the reconstruction processing. Similarly, the second data may be projection data that indicates a distribution of X-ray intensity and X-ray energies on a detection plane of the X-ray detector 12, or may be CT image data subjected to the reconstruction processing. Hereinafter, the first data in a state of projection data is denoted as first projection data, and the second data in a state of projection data is denoted as second projection data. Moreover, the first data in a state of CT image data is denoted as first CT image data, and the second data in a state of CT image data is denoted as second CT image data.

For example, the generating function 44*c* reconstructs the first CT image data based on the first projection data. The first CT image data is a monochrome image having no energy information. The method of reconstructing the first CT image data is not particularly limited, but any technique can be adopted. For example, the generating function 44*c* generates an X-ray CT image by performing reconstruction processing using the filtered back-projection method, the iterative-approximation reconstruction method, or the like with respect to the first projection data.

Moreover, the generating function 44*c* reconstructs a photon-counting CT image that shows a spatial distribution of a base material as the second CT image data based on the second projection data. For example, the generating function 44*c* first acquires data of response function indicating detector response characteristics. Such response function data can be generated by calculating a response of a standard detection system (that is, a detection energy and a detection intensity) with respect to plural monochromatic X-rays having plural incident X-ray energies by predictive calculation, an experiment, and a combination of predictive calculation and experiment, and generated based on a measurement value of the detection energy and the detection intensity. The response function data may be generated based on a measurement value of actual measurement acquired in calibration or the like. The response function defines a relationship between a detection energy of each incident X-ray and an output response of a system. For example, the response function defines a relationship between a detection energy of each incident X-ray and a detection intensity. The generated response function is stored in, for example, the memory 41.

Furthermore, the generating function 44*c* calculates an X-ray absorption amount of each of plural base materials based on count data about the plural energy bins, an energy spectrum of an incident X-ray to the subject P, and the response function stored in the memory 41. The generating function 44*c* can calculate an X-ray absorption amount that is not affected by response characteristics of the X-ray detector 12 and the DAS 18 by calculating the X-ray absorption amount by using the response function and based on the count data and the energy spectrum of an incident X-ray to the subject P. The processing of thus acquiring an X-ray absorption amount for each base material is called material decomposition. As base materials, various materials, such as calcium, calcification, bone, fat, muscle, air, organ, lesion, hard tissue, soft tissue, and contrast agent, can be set. A base material subject to calculation may be determined in advance by an operator or the like through the input interface 43. The X-ray absorption amount indicates an amount of X-ray to be absorbed by a base material. For example, the X-ray absorption amount is determined by a combination of an X-ray attenuation coefficient and an X-ray transmission path length.

The generating function 44*c* reconstructs a photon-counting CT image that shows a spatial distribution of a base material to be imaged out of the plural base materials based on the X-ray absorption amount of each of the base materials, and stores the generated CT image data in the memory 41. The base material to be imaged may be one kind or more. The kind of the base material to be imaged may be determined by a user through the input interface 43.

As described above, the generating function 44*c* respectively reconstructs the first CT image data and the second CT image data. If these CT image data are compared, the first CT image data that is reconstructed using information of more views has higher spatial resolution. Moreover, while the first CT image data is a monochrome image, the second CT image data is a color image that shows energy information, such as a spatial distribution of a base material. The generating function 44*c* can generate third data by subjecting the first CT image data having high spatial resolution and the second CT image data being a color image to, for example, pan sharpening processing. In this case, the third data is to be a color image data having high spatial resolution.

Data sizes of each pixel of the first data and the second data are approximately the same. In the following, a case in which the count temporary-storage circuitry 184 outputs the stored count data as a data packet in a certain format at the time when the count data from the four counting circuits illustrated in FIG. 2 and FIG. 3 is stored will be explained.

Figure 5:
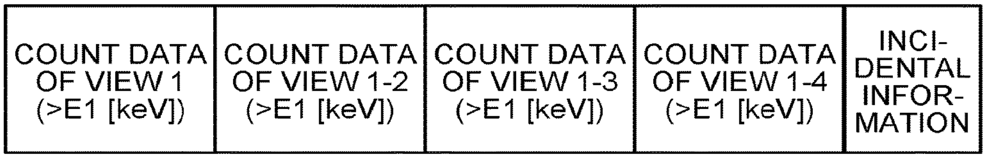
FIG. 5 is a diagram illustrating a data packet according to the first embodiment.

For example, the first data acquired in the resolution priority mode is output from the count temporary-storage circuitry 184 in a packet format illustrated in FIG. 5. The packet in FIG. 5 is constituted of a fragment including the count data of "view 1", which is output data from the counting circuitry 183*a*, a fragment including the count data of "view 1-2", which is output data from the counting circuitry 183*b*, a fragment including the count data of "view 1-3", which is output data from the counting circuitry 183*c*, a fragment including the count data of "view 1-4", which is output data from the counting circuitry 183*d*, and incidental information. That is, the packet in FIG. 5 is data in which the sampling intervals are short, having information of four views. All the count data included in the packet in FIG. 5 are counted using "E1 [keV]" as the threshold, and does not include energy information for each energy bin. The incidental information includes, for example, information such as the trigger distribution settings and the reference signal settings.

That is, the first data that is output from the count temporary-storage circuitry 184 is constituted of at least a first fragment and a second fragment, and the first fragment contains data corresponding to a first view, and a second fragment contains data including the second view that is different from the first view. For example, the first data illustrated in FIG. 5 includes the first fragment including the count data of "view 1" and the second fragment including the count data of "view 1-2". The first fragment contains data corresponding to the first view "view 1". The second fragment contains data corresponding to a view "view 1-2" including the second view "view 2".

Figures 6, 7:
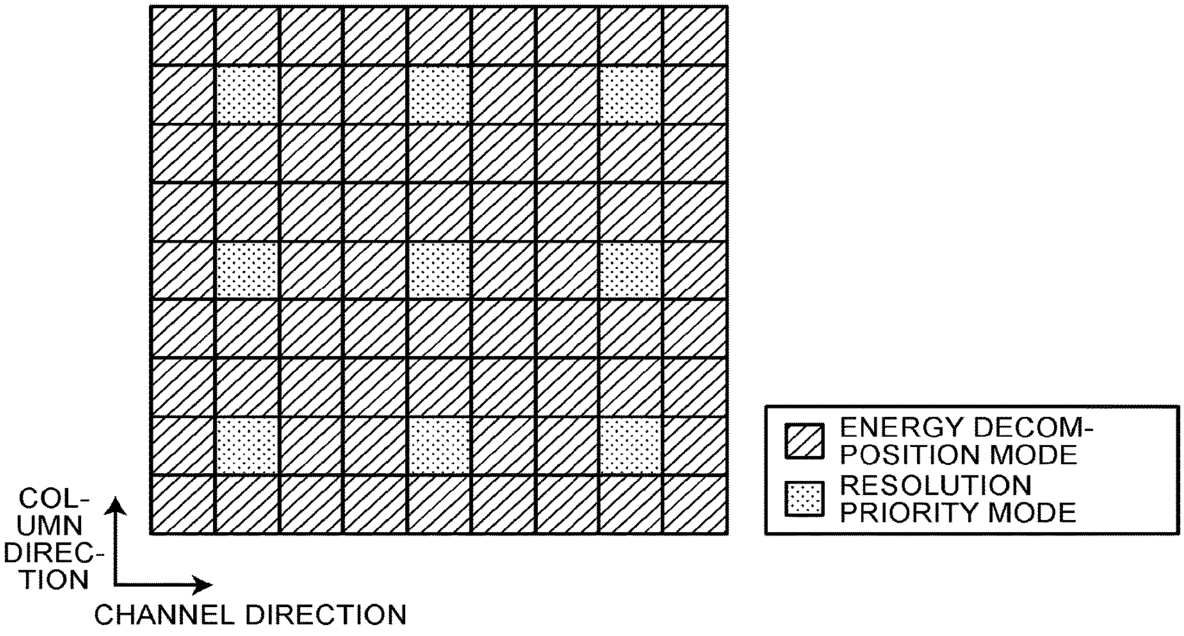
FIG. 6 is a diagram illustrating a data packet according to the first embodiment.
FIG. 7 is an example of a method of setting the resolution priority mode and the energy decomposition mode for each pixel according to the first embodiment.

Moreover, the second data acquired in the energy decomposition mode is output from the count temporary-storage circuitry 184 in a packet format illustrated in FIG. 6. The packet in FIG. 6 is constituted of a fragment including the count data of ">E1 [keV]", which is output data from the counting circuitry 183*a*, a fragment including the count data of ">E2 [keV]", which is output data form the counting circuitry 183*b*, a fragment including the count data of ">E3 [keV]", which is output data from the counting circuitry 183*c*, a fragment including the counting data of ">E4 [keV]", which is output data from the counting circuitry 183*d*, and incidental information. That is, the packet in FIG. 5 is data including energy information. All the count data included in the packet in FIG. 5 are data acquired about the view "view 1-4", and the sampling intervals are long compared to the first data.

That is, the second data output from the count temporary-storage circuitry 184 is constituted of at least a third fragment and a fourth fragment, and the third fragment contains data corresponding to a first energy, and the fourth fragment contains data corresponding to a second energy that is different from the first energy. For example, the second data illustrated in FIG. 6 includes the third fragment including the count data counted using an energy "E1 [keV]" as the threshold, and the fourth fragment including the count data counted using an energy "E2 [keV]" as the threshold. The third fragment contains data corresponding to the first energy "E1 [keV]". The fourth fragment contains data corresponding to the second energy "E2 [keV]" that is different from the first energy "E1 [keV]".

As described above, the X-ray CT apparatus 1 of the first embodiment includes the X-ray detector 12, the acquisition function 44*b*, and the generating function 44*c*. The X-ray detector 12 is a photon counting X-ray detector that is constituted of plural pixels. The acquisition function 44*b* acquires the first data in the resolution priority mode from the first pixel set out of the plural pixels in the X-ray detector 12. Moreover, the acquisition function 44*b* acquires the second data in the energy decomposition mode from the second pixel set that is different from the first pixel set out of the plural pixels in the X-ray detector 12 at longer sampling intervals than those in the resolution priority mode. The generating function 44*c* generates the third data based on the first data and the second data. Thus, the X-ray CT apparatus 1 of the first embodiment can provide a high resolution color image.

As another method of providing a high resolution color image, similarly to the conventional method, shortening sampling intervals while driving all pixels of an X-ray detector in the energy decomposition mode is conceivable. However, data acquired in the energy decomposition mode has a large data size as it contains energy information, and when the sampling intervals are shortened, to further increase the data size, time required for transmission and processing of data increases. Furthermore, time required for reconstructing CT image data and until it is output as an image increases to be long.

On the other hand, in the X-ray CT apparatus 1 of the first embodiment, the sampling intervals are long when the second data is acquired in the energy decomposition mode, and increase in data size is not caused. Although the sampling intervals are short when the first data is acquired in the resolution priority mode, the first data is data not including energy information, and as illustrated in FIG. 5 and FIG. 6, the data size of each pixel is approximately the same as the second data. As described above, the X-ray CT apparatus 1 of the first embodiment can provide a color image with improved resolution while preventing increase of time required until output of an image.

For example, in a clinical setting, when accurate detection of changes in cardiac morphology is desired (at the time of dynamic scanning), or when imaging of a calculus with high spatial resolution is desired, it is required to reduce sampling intervals to improve resolution of CT image data. On the other hand, when changes in cardiac morphology is to be captured while injecting a contrast agent or the like, it is preferable to maintain the material decomposition capability by acquiring the energy information. According to the X-ray CT apparatus 1 of the first embodiment, a color image with improved resolution can be provided while preventing increase of time required until output of an image and, therefore, various requirements in a clinical setting as described can be satisfied.

The first embodiment has been explained using FIG. 1 to FIG. 6, but these are only one example, and various modifications are possible.

For example, in the example in FIG. 4, the energy decomposition mode is set for the pixel, the pixel number in a column direction of which is "3n−1" and the pixel number in the channel direction of which is "3m−1", and the resolution priority mode is set for other pixels. That is, a ratio between the first pixel set acquired in the resolution priority mode and the second pixel set acquired in the energy decomposition mode is "8:1", and the number of pixels included in the second pixel set is small. The ratio between the first pixel set and the second pixel set can be changed appropriately. For example, when the material decomposition capability is desired to be maintained high, the number of pixels included in the second pixel set can be increased as illustrated in FIG. 7.

Moreover, the example of generating the third data by pan sharpening processing has been explained, but embodiments are not limited thereto. For example, the generating function 44*c* may generate the third data by inputting the first CT image data and the second CT image data described previously to a trained model that has a function of accepting a monochrome image with high resolution and a color image with low resolution, to generate a color image with high resolution. Such a trained model is constituted of, for example, a neural network (NN).

The trained model may be generated by the generating function 44*c*, or may be generated by another device different from the X-ray CT apparatus 1. For example, the generating function 44*c* can generate the trained model by training a neural network using an image obtained by acquiring all pixels in the X-ray detector 12 in the resolution priority mode and an image obtained by acquiring all pixels in the X-ray detector 12 in the energy decomposition model as training data.

Furthermore, the example in which the first pixel set and the second pixel set are arranged uniformly in a certain pattern has been explained in FIG. 4 and FIG. 7, but nonuniform arrangement is also possible. That is, arrangement of the first pixel set and the second pixel set may have locality.

For example, the acquisition function 44*b* may determine the arrangement of the first pixel set and the second pixel set according to a region of interest in the subject P. For example, in dynamic scanning of the heart at the time of injection of a contrast agent, the heart of the subject P is to be the region of interest. Furthermore, in interventional radiology (IVR), a portion around a distal end of a catheter that is inserted into the body of the subject P and is operated by a user, such as a doctor, is to be the region of interest. The acquisition function 44*b* determines the arrangement of the first pixel set and the second pixel set such that more pixels at a position corresponding to a region of interest in the channel direction are set to the energy decomposition mode, for example, as illustrated in FIG. 8 and FIG. 9.

Figure 8:
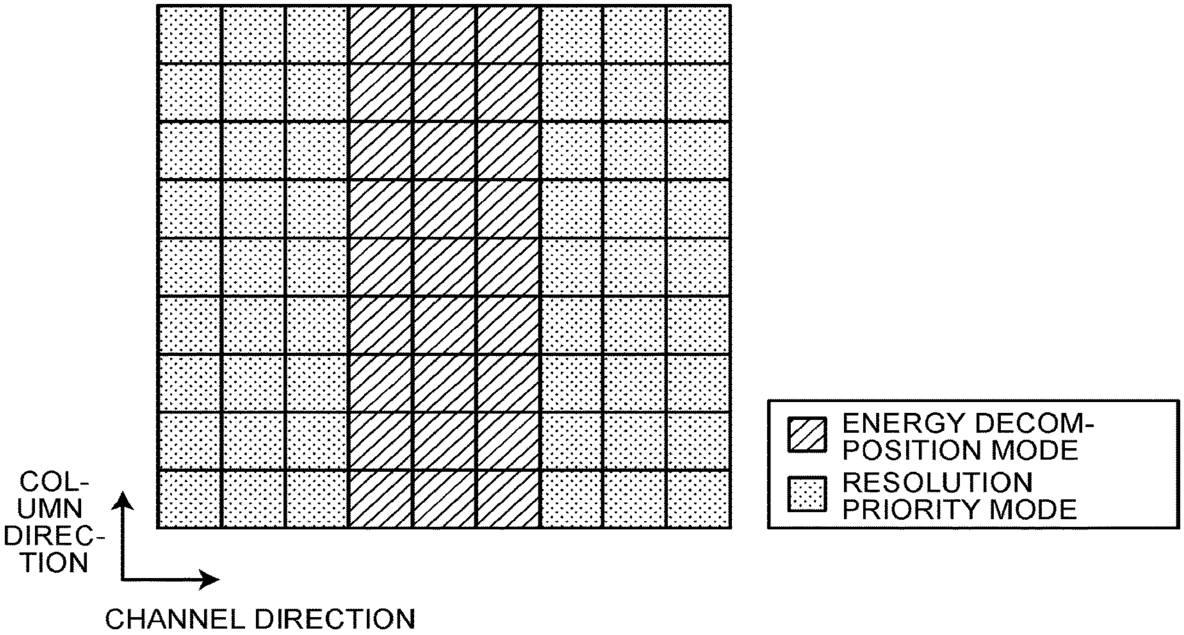
FIG. 8 is an example of a method of setting the resolution priority mode and the energy decomposition mode for each pixel according to the first embodiment.
Figure 9:
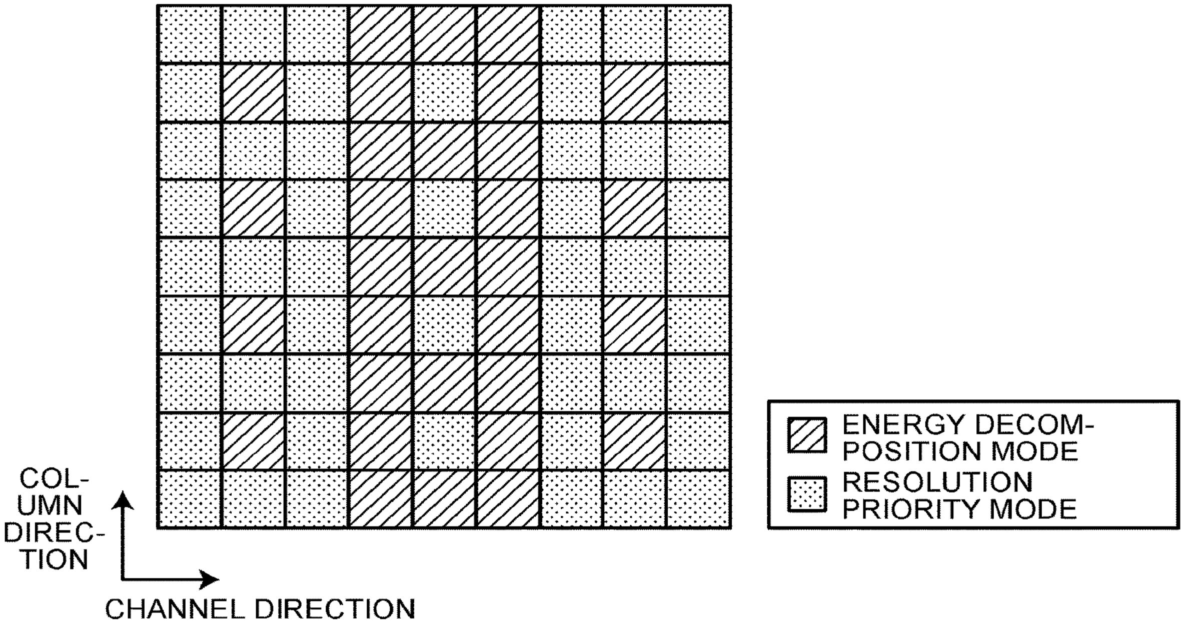
FIG. 9 is an example of a method of setting the resolution priority mode and the energy decomposition mode for each pixel according to the first embodiment.

In the example illustrated in FIG. 8 and FIG. 9, it is possible to maintain the material decomposition capability by acquiring more energy information of the heart of the subject P, for example, in the dynamic scanning of the heart at the time of injection of a contrast agent. By then performing the material decomposition for a base material, such as iodine included in a contrast agent, an image in which the contrast agent flowed into the heart is clearly shown can be obtained. Moreover, for example, in IVR, it is possible to maintain the material decomposition capability by acquiring more energy information of a portion near the distal end of a catheter. By using the energy information, for example, a guide wire at the distal end of the catheter can be detected easily.

The region of interest may be set based on an image of the subject P that has been acquired in advance. For example, before CT scanning (main scanning) of acquiring an image for diagnosis, acquisition of positioning image data (scano-image data) is performed, targeting the subject P laid on the tabletop 33. Furthermore, for the purpose of disease progression monitoring or the like, there is a case that main scanning is performed multiple times with respect to the same subject P. As described, there is a case of acquiring a different image of the subject P before starting CT scanning with respect to the subject P, and the image is stored in the memory 41, or in a picture archiving and communication system (PACS). The acquisition function 44*b* can acquire the image of the subject P acquired in advance from the memory 41 or PACS, and can set the region of interest based on the acquired image.

For example, the output function 44*d* displays an image of the subject P acquired in advance on the display 42. The acquisition function 44*b* then accepts an input operation from a user that has referred to the image through the input interface 43, and thereby sets a region of interest.

As another example, the acquisition function 44*b* may set a region of interest by performing image processing with respect to the image of the subject P acquired in advance. For example, the acquisition function 44*b* detects an organ such as the heart, and a device such as a catheter by arbitrary image processing such as pattern matching, and can set a region of interest so as to include the detected organ and the device. The acquisition function 44*b* may determine the arrangement of the first pixel set and the second pixel set automatically according to the set region of interest. That is, the acquisition function 44*b* can switch modes of the respective pixels automatically from the image of the subject P acquired in advance.

The image of the subject P used for setting a region of interest is not limited to CT image data, but may be one acquired by a different kind of medical image processing apparatus (for example, an X-ray diagnostic apparatus, a magnetic resonance imaging (MRI) apparatus, an ultrasound diagnostic apparatus, a single photon emission computed tomography (SPECT) apparatus, a positron emission computed tomography (PET) apparatus, and the like).

Figure 10:
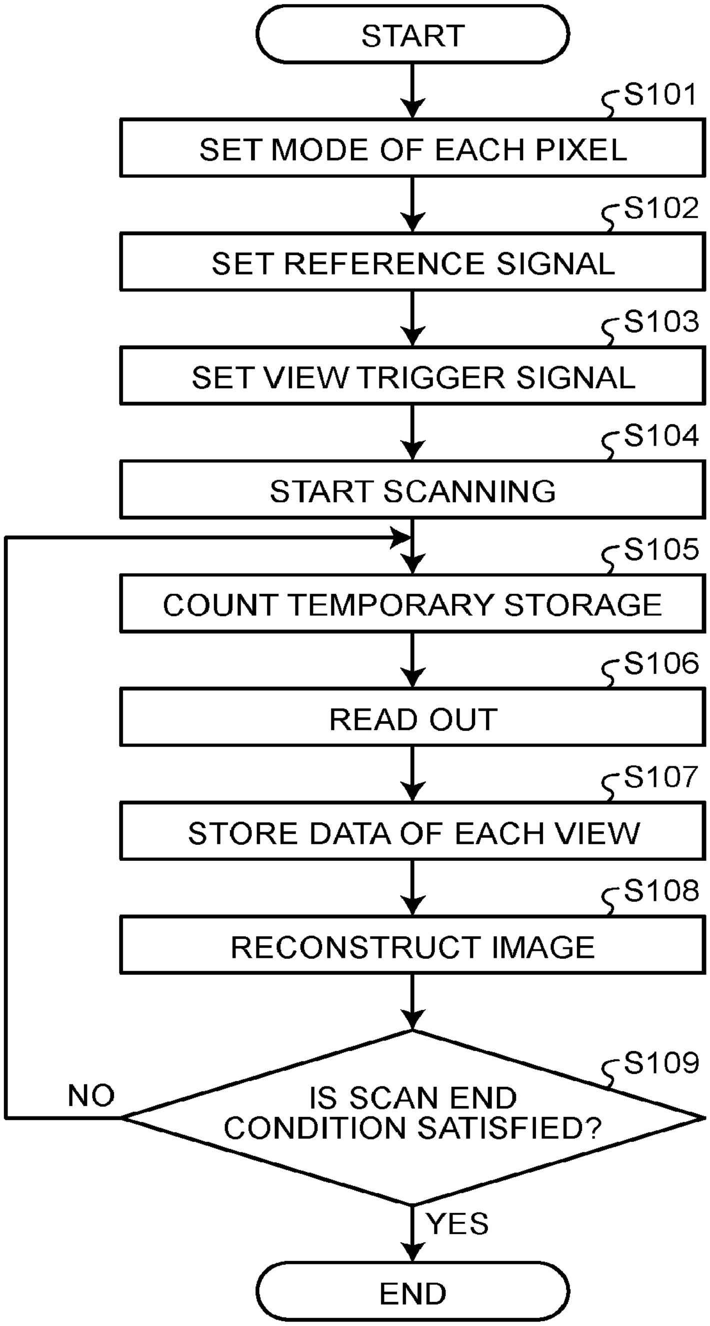
FIG. 10 is a flowchart illustrating a series of processing of the X-ray CT apparatus according to the first embodiment.

Next, a flow of processing until the first data and the second data are acquired will be explained using FIG. 10. FIG. 10 is a flowchart illustrating a series of processing of the X-ray CT apparatus 1 according to the first embodiment.

First, the acquisition function 44*b* sets the modes of the respective pixels (step S101). That is, the acquisition function 44*b* determines the arrangement of the first pixel set for which acquisition is performed in the resolution priority mode and the second pixel set for which acquisition is performed in the energy decomposition mode.

Moreover, the acquisition function 44*b* sets the reference signal (step S102). The acquisition function 44*b* respectively sets the reference signal corresponding to the first pixel set and the reference signal corresponding to the second pixel set. For example, the acquisition function 44*b* sets specific values of the reference signals "E1 [keV]" to "E4 [keV]" illustrated in FIG. 2 and FIG. 3. The reference signal may be set by an input of a user, or may be set automatically by the acquisition function 44*b* according to a part subject to treatment.

Furthermore, the acquisition function 44*b* sets the view trigger signal (step S103). The acquisition function 44*b* respectively sets the view trigger signal corresponding to the first pixel set and the view trigger signal corresponding to the second pixel set. For example, the acquisition function 44*b* sets specific values of the view trigger signals "V1" to "V4" illustrated in FIG. 2. That is, the acquisition function 44*b* sets sampling intervals respectively in the energy decomposition mode and the resolution priority mode. The view trigger signal may be set by an input of a user, or may be set automatically by the acquisition function 44*b* according to a part subject to treatment.

After setting of scanning conditions indicated at step S101 to step S103 is completed, the acquisition function 44*b* controls operation of the X-ray high-voltage device 14, the controller 15, the DAS 18, the bed driving device 32, and the like in a state in which the subject P is laid on the tabletop 33, and starts CT scanning (step S104). While CT scanning is being performed, each of the counting circuitry 183*a* to 183*d* stores the count data in the internal memory of the count temporary-storage circuitry 184 according to the view trigger signal distributed by the trigger distribution circuitry 182 (step S105). The count temporary-storage circuitry 184 reads all of the stored count data from the internal memory at the time when the count data is input from all of the counting circuitry (the counting circuitry 183*a* to 183*d*), to output to the console 40 (step S106). Thus, data for each view (the first projection data and the second projection data) is stored in the memory 41 (step S107).

The generating function 44*c* performs image reconstruction based on the data stored in the memory 41 at step S107 (step S108). That is, the generating function 44*c* can perform image reconstruction by sequentially using the acquired projection data during the CT scanning. Moreover, the acquisition function 44*b* determines whether a scan end condition is satisfied (step S109). For example, the acquisition function 44*b* determines whether an entire part of a predetermined scan range has been scanned. When the scan end condition is not satisfied (step S109: NO), it shifts to step S105, and the processing at step S105 to step S108 is repeated. On the other hand, when the scan end condition is satisfied (step S109: YES), the CT scanning is ended.

In FIG. 10, generation of the third data based on the first data and the second data can be performed between step S108 and step S109. That is, the generating function 44*c* can sequentially generate the third data by using the first CT image data and the second CT image data sequentially reconstructed, during the CT scanning. Alternatively, generation of the third data based on the first data and the second data may be performed after the CT scanning is finished.

In the first embodiment described above, the example in which the first data is acquired in the resolution priority mode from the first pixel set, and the second data is acquired in the energy decomposition mode from the second pixel set has been explained. On the other hand, in a second embodiment, an example in which the first data is acquired in a first mode using the first view trigger signal from the first pixel set and a second data is acquired in the second mode using the second view trigger signal from the second pixel set will be explained. In the following, a point that differs from the first embodiment will be explained, and components similar to those of the first embodiment will be denoted by common reference symbols, and explanation thereof will be omitted.

Figure 11:
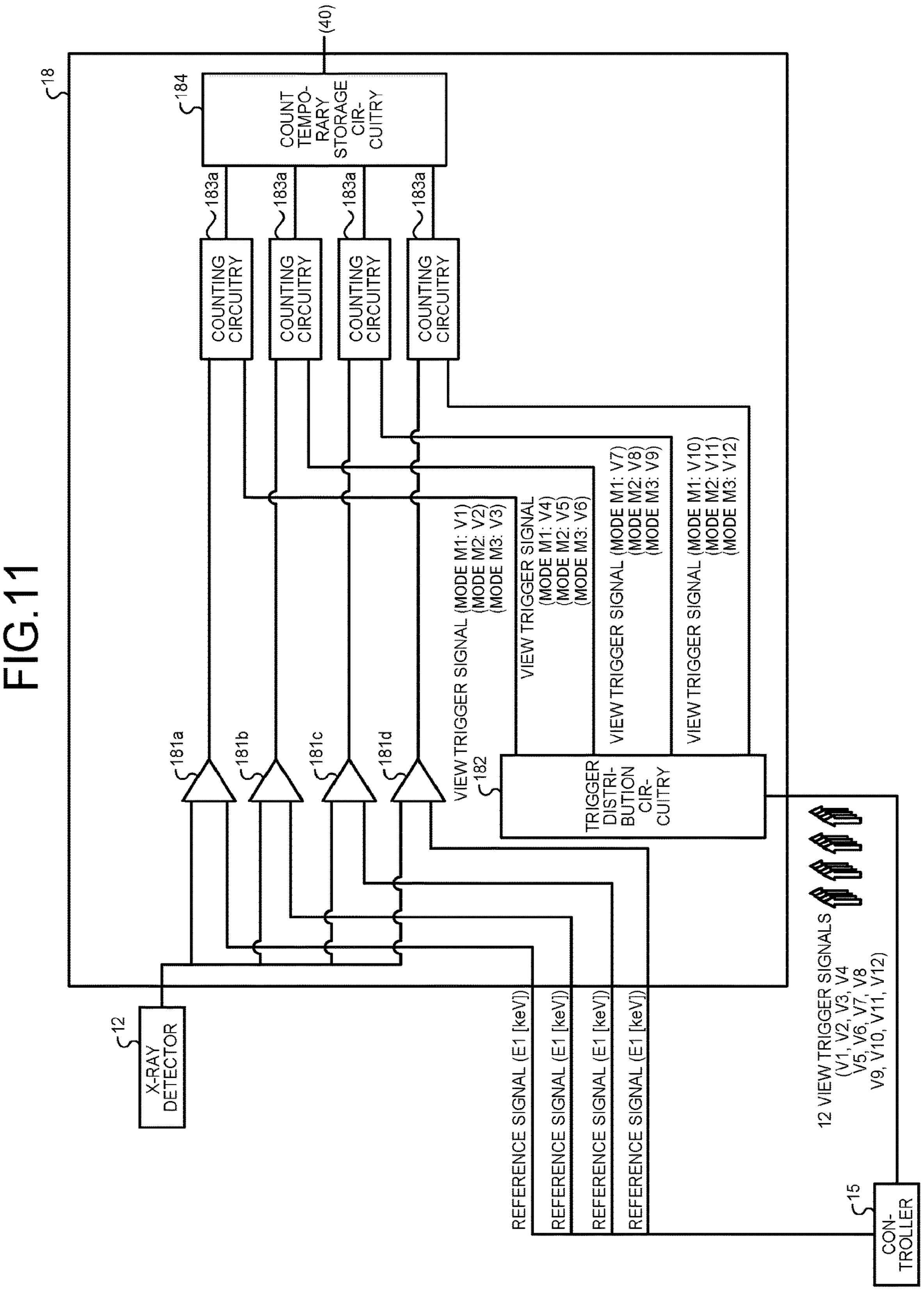
FIG. 11 is a diagram illustrating a configuration example of a DAS according to a second embodiment.

The first view trigger signal and the second view trigger signal according to the second embodiment will be explained using FIG. 11. As illustrated in FIG. 11, the configuration of the DAS 18 itself is similar to the DAS 18 according to the first embodiment illustrated in FIG. 2 and FIG. 3.

In an example in FIG. 11, to plural comparators, the reference signal "E1 [keV]" is equally provided. That is, data acquired in the example in FIG. 11 does not include energy information.

In the example in FIG. 11, to the trigger distribution circuitry 182, 12 view trigger signals (V1, V2, V3, V4, V5, V6, V7, V8, V9, V10, V11, V12) are input from the controller 15. The trigger distribution circuitry 182 respectively provides these 12 view trigger signals to the counting circuitry 183*a* to 183*d* according to the mode set thereto.

For example, when a mode M1 is set, the trigger distribution circuitry 182 provides the view trigger signal "V1" to the counting circuitry 183*a*, provides the view trigger signal "V4" to the counting circuitry 183*b*, provides the view trigger signal "V7" to the counting circuitry 183*c*, and provides the view trigger signal "V10" to the counting circuitry 183*d*. The respective counting circuitry read the count data accumulated in the internal memory upon receiving the provided view trigger signal. According to the mode M1, similarly to the resolution priority mode illustrated in FIG. 3, the counting data is read at short sampling intervals.

Moreover, when a mode M2 is set, the trigger distribution circuitry 182 provides the view trigger signal "V2" to the counting circuitry 183*a*, provides the view trigger signal "V5" to the counting circuitry 183*b*, provides the view trigger signal "V8" to the counting circuitry 183*c*, and provides the view trigger signal "V11" to the counting circuitry 183*d*. The respective counting circuitry read the count data accumulated in the internal memory upon receiving the provided view trigger signal. The mode M2 has the same count acquisition period (sampling intervals for each pixel) as the mode M1, but has different timings of reading the count data therefrom.

Furthermore, when a mode M3 is set, the trigger distribution circuitry 182 provides the view trigger signal "V3" to the counting circuitry 183*a*, provides the view trigger signal "V6" to the counting circuitry 183*b*, provides the view trigger signal "V9" to the counting circuitry 183*c*, and provides the view trigger signal "V12" to the counting circuitry 183*d*. The respective counting circuitry read the count data accumulated in the internal memory upon receiving the provided view trigger signal. The mode M3 has the same count acquisition period as the mode M1 and the mode M2, but has different timings of reading the count data therefrom.

Figure 12:
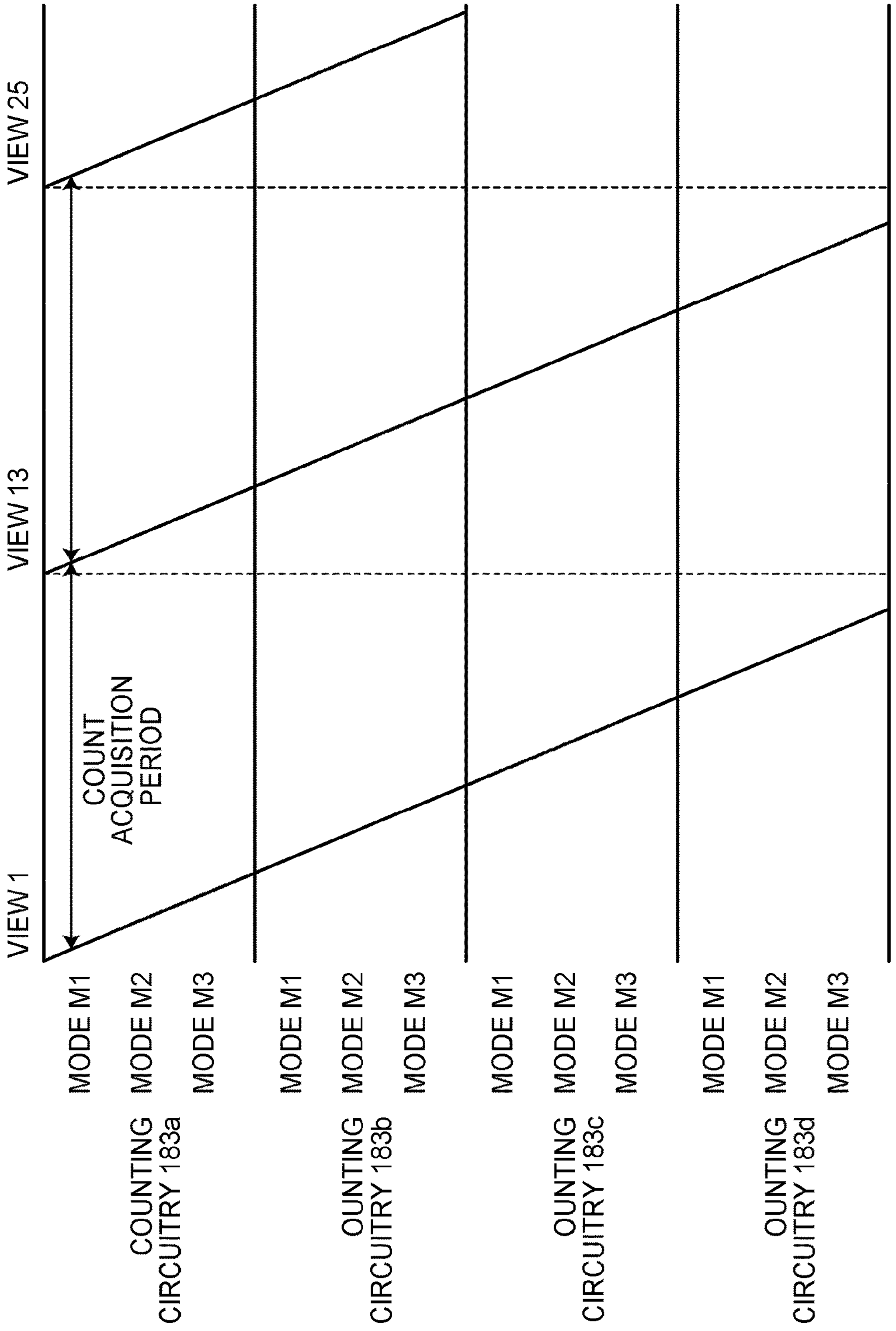
FIG. 12 is a diagram for explaining read timing of count data according to the second embodiment.

Readout timing of the count data in each mode will be explained using FIG. 12. A horizontal axis in FIG. 12 indicates the number of views and corresponds to a time axis. For example, when the mode M1 is set, the counting circuitry 183*a* reads out the count data in timing of "view 1", and reads out again, after the count acquisition period for "12 views" has passed, the count data in timing of "view 13". Furthermore, the counting circuitry 183*a* reads out again, after the count acquisition period for "12 views" has passed, the count data in timing of "view 25". On the other hand, when the mode M2 is set, the counting circuitry 183*a* reads out the count data in timing of "view 2", and reads again, after the count acquisition period for "12 views" has passed, the count data in timing of "view 14". Furthermore, the counting circuitry 183*a* reads out again, after the count acquisition period for "12 views" has passed, the count data in timing of "view 26".

Moreover, for example, when the mode M3 is set, the counting circuitry 183*a* reads out the count data in timing of "view 3", and reads again, after the count acquisition period for "12 views" has passed, the count data in timing of "view 15". Furthermore, the counting circuitry 183*a* reads out again, after the count acquisition period for "12 views" has passed, the count data in timing of "view 27". As described, the mode M1, the mode M2, and the mode M3 have the same count acquisition period but have different timings of reading out the count data (views).

For example, out of the plural pixels of the X-ray detector 12, the first mode (for example, the mode M1) is set to the first pixel set. In the first mode, the first data is acquired by using the first view trigger signal, such as the view trigger signals "V1", "V4", "V7", and "V10", illustrated in FIG. 11. Moreover, out of the plural pixels, the second mode (for example, the mode M2 or the mode M3) is set to the second pixel set, which is different from the first pixel set. When the second mode is the mode M2, the second data is acquired by using the second view trigger signal, such as the view trigger signals "V2", "V5", "V8", and "V11". When the second mode is the mode M3, the second data is acquired by using the second view trigger, such as the view triggers "V3", "V6", "V9", and "V12".

By performing acquisition in the mode M1 to the mode M3, substantial sampling intervals can be further shortened compared to the resolution priority mode explained in FIG. 3. For example, if it is assumed that readout of the count data is performed every "3 views" by the processing in FIG. 3 is assumed, readout of the count data can be performed every "1 view" by the processing in FIG. 11. Therefore, the generating function 44*c* can reconstruct CT image data with higher resolution as the third data based on the first data and the second data.

Moreover, the count acquisition period (sampling intervals for each pixel) is not increased from that in the processing in FIG. 3 and, therefore, increase of the data size is also avoided. That is, according to the X-ray CT apparatus 1 of the second embodiment, resolution can be improved while preventing increase of time required until output of an image. Thus, for example, in a case in which high spatial resolution is required, such as in evaluation of vascular calcification, CT image data with high special resolution can be provided while preventing increase of time required until output of an image.

Figure 13:
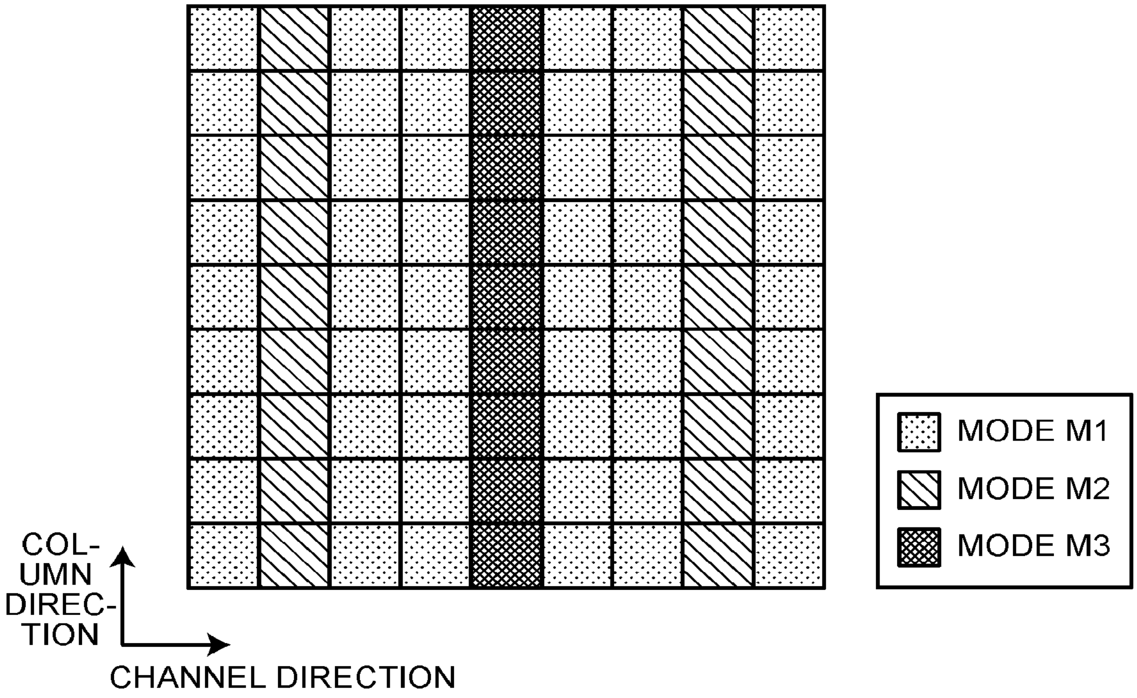
FIG. 13 is an example of a method of setting multiple modes for each pixel according to the second embodiment.

For example, the acquisition function 44*b* sets the mode M1, the mode M2, and the mode M3 to the pixels of the X-ray detector 12 such that the mode changes in the channel direction as illustrated in FIG. 13. That is, the acquisition function 44*b* determines the arrangement of the first pixel set and the second pixel set such that the mode changes in the channel direction. By arranging pixels of different modes in the channel direction (that is, in a rotation direction of the X-ray detector 12), it can be regarded that intervals between pixels in the rotation direction are not uniform. Therefore, when converting the count distribution of each pixel into a frequency distribution, it is possible to extract components beyond the Nyquist frequency.

Figure 14:
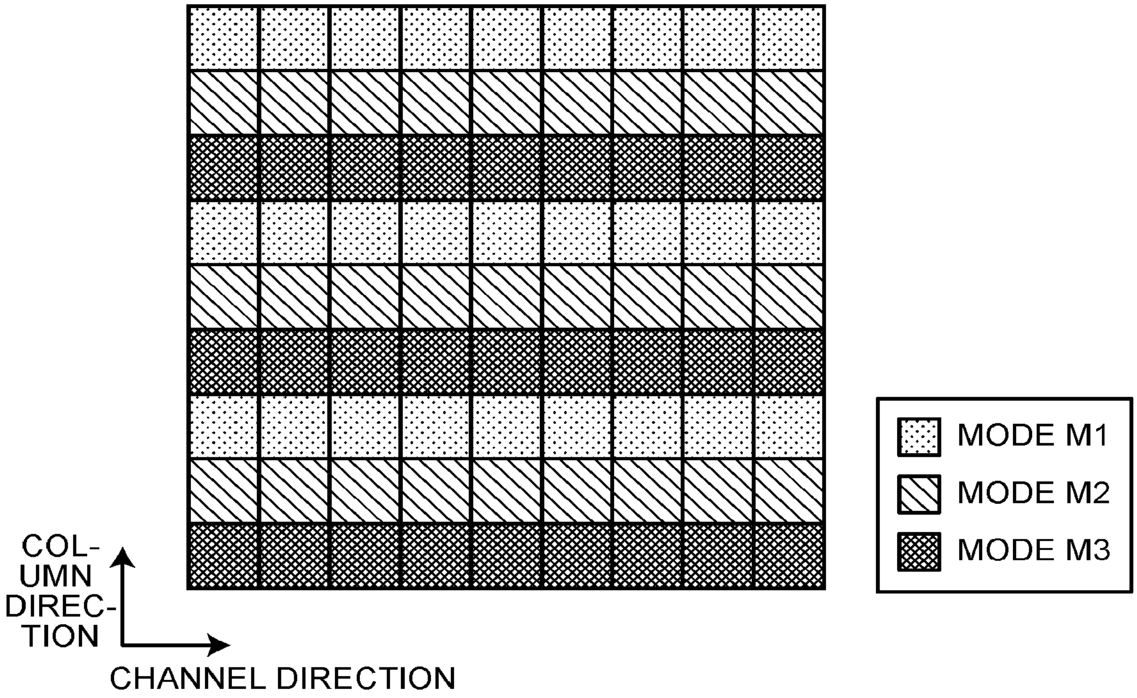
FIG. 14 is an example of a method of setting multiple modes for each pixel according to the second embodiment.

Furthermore, for example, the acquisition function 44*b* sets the mode M1, the mode M2, and the mode M3 to the pixels of the X-ray detector 12 such that the mode changes in the column direction as illustrated in FIG. 14. That is, the acquisition function 44*b* sets the arrangement of the first pixel set and the second pixel set such that the mode changes in the column direction. Thus, a frequency distribution with phases that vary for respective columns can be obtained and, therefore, by combining images of the respective columns also, it becomes possible to obtain high-definition slice images.

In FIG. 11 to FIG. 14, it has been explained that a mode in which the count using only the single reference signal "E1 [keV]" is performed is set to all pixels. That is, a case in which energy information is not acquired in any pixel has been explained. However, embodiments are not limited thereto, and data may be acquired in the energy decomposition mode in some of the pixels similarly to the first embodiment. For example, for a pixel set to which the mode M3 is set in FIG. 13 and FIG. 14, the energy decomposition mode may be set. Furthermore, the X-ray detector 12 has been explained as a photon-counting detector, but when the energy decomposition mode is not to be set, the X-ray detector 12 may be an energy integrating detector.

A term "processor" used in the above explanation signifies a circuit, such as a central processing unit (CPU), a graphical processing unit (GPU), an ASIC, a programmable logic device (for example, simple programmable logic device (SPLD), complex programmable logic device (CPLD)), and a field programmable gate array (FPGA). For example, when the processor is a CPU, the processor implements a function by reading and executing a program stored in a storage circuit. On the other hand, for example, when the processor is an ASIC, instead of storing a program in the storage circuit, the function is directly installed as a logic circuit in a circuit of the processor. The respective processors of the embodiments are not limited to be configured as a single circuit for each processor, but may be configured by combining plural independent circuits as one processor, to implement its function. Furthermore, it may be configured to implement its function by integrating plural components in the respective drawings into one processor.

The respective components of the respective devices according to the embodiments described above are of functional concept, and it is not necessarily required to be configured physically as illustrated. That is, specific forms of distribution and integration of the respective devices are not limited to the ones illustrated, and all or some thereof can be configured to be distributed or integrated functionally or physically in arbitrary units according to various kinds of loads, usage conditions, and the like. Furthermore, as for the respective processing functions performed by the respective devices, all or an arbitrary part thereof can be implemented by a CPU and a computer program that is analyzed and executed by the CPU, or can be implemented as hardware by wired logic.

Moreover, the method explained in the embodiments described above can be implemented by executing a program that has been prepared in advance by a computer such as a personal computer and a workstation. This program can be distributed through a network such as the Internet. Furthermore, this program can be recorded on a computer-readable non-transient recording medium, such as a hard disk, a flexible disk (FD), a compact-disk read-only memory (CD-ROM), a magneto optical disk (MO), and a digital versatile disk (DVD), and can be executed by being read by a computer from the recording medium.

According to at least one of the embodiments explained above, resolution can be improved while preventing increase of time required until output of an image.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray CT apparatus comprising:

a photon-counting X-ray detector including a plurality of pixels; and processing circuitry configured to set a resolution priority mode or an energy decomposition mode for each pixel, acquire first data in the resolution priority mode from a first pixel set out of the pixels, acquire second data in the energy decomposition mode from a second pixel set, which is different from the first pixel set, out of the pixels at sampling intervals longer than those of the resolution priority mode, and generate third data based on the first data and the second data.

2. The X-ray CT apparatus according to claim 1, wherein the first data is constituted of at least a first fragment and a second fragment, and the first fragment contains data corresponding to a first view, and a second fragment contains data corresponding to a view that includes a second view, which is different from the first view.

3. The X-ray CT apparatus according to claim 2, wherein the data contained in the first fragment and the data contained in the second fragment correspond to the same energy.

4. The X-ray CT apparatus according to claim 1, wherein the second data is constituted of at least a third fragment and a fourth fragment, and the third fragment contains data corresponding to a first energy, and the fourth fragment contains data corresponding to a second energy, which is different from the first energy.

5. The X-ray CT apparatus according to claim 4, wherein the data contained in the third fragment and the data contained in the fourth fragment correspond to the same view.

6. The X-ray CT apparatus according to claim 1, wherein the processing circuitry is further configured to reconstruct first CT image data from first projection data that is acquired in the resolution priority mode from the first pixel set, reconstruct second CT image data from second projection data that is acquired in the energy decomposition mode from the second pixel set, and generate the third data based on the first CT image data and the second CT image data.

7. The X-ray CT apparatus according to claim 1, wherein the processing circuitry is further configured to determine arrangement of the first pixel set and the second pixel set according to a region of interest in a subject.

8. The X-ray CT apparatus according to claim 7, wherein the processing circuitry is further configured to set the region of interest based on an image of the subject acquired in advance, and determine arrangement of the first pixel set and the second pixel set according to the set region of interest.

9. The X-ray CT apparatus according to claim 8, wherein the processing circuitry is further configured to set the region of interest by performing image processing with respect to the image.

10. The X-ray CT apparatus according to claim 1 further comprising comparators connected in parallel with respect to the photon-counting X-ray detector and trigger distribution circuitry connected to counting circuitry, wherein the processing circuitry acquires the first data and the second data by controlling reference signals provided to the comparators and view trigger signals provided by the trigger distribution circuitry.

11. An X-ray CT apparatus comprising:

an X-ray detector including a plurality of pixels;

counting circuitry configured to accumulate a signal output by each of the pixels according to an incident X-ray as count data, and perform readout of the accumulated count data, upon receiving a view trigger signal; and processing circuitry configured to acquire first data in a first mode using a first view trigger signal from a first pixel set out of the pixels, acquire second data in a second mode using a second view trigger signal from a second pixel set, which is different from the first pixel set, out of the pixels in a count acquisition period same as the first mode, and generate third data based on the first data and the second data.

12. The X-ray CT apparatus according to claim 11, wherein the processing circuitry is further configured to determine arrangement of the first pixel set and the second pixel set such that a mode changes in a channel direction in the X-ray detector.

13. The X-ray CT apparatus according to claim 11, wherein the processing circuitry is further configured to determine arrangement of the first pixel set and the second pixel set such that a mode changes in a column direction in the X-ray detector.

14. An X-ray CT apparatus comprising:

a photon-counting X-ray detector including a plurality of pixels; and processing circuitry configured to acquire first data in a resolution priority mode from a first pixel set out of the pixels, acquire second data in an energy decomposition mode from a second pixel set, which is different from the first pixel set, out of the pixels at sampling intervals longer than those of the resolution priority mode, and generate third data based on the first data and the second data, wherein the processing circuitry determines arrangement of the first pixel set and the second pixel set according to a region of interest in a subject.

* * * * *